United States Patent [19]

Mihailowitsch

[11] Patent Number: 5,378,147
[45] Date of Patent: Jan. 3, 1995

[54] VENTRAL TELESCOPE

[75] Inventor: Franz-Josef Mihailowitsch, Bochum, Germany

[73] Assignee: H. Michael Hartmann, River Forest, Ill.

[21] Appl. No.: 962,199

[22] PCT Filed: Mar. 13, 1992

[86] PCT No.: PCT/EP92/00563

§ 371 Date: Dec. 21, 1992

§ 102(e) Date: Dec. 21, 1992

[87] PCT Pub. No.: WO92/19174

PCT Pub. Date: Nov. 12, 1992

[30] Foreign Application Priority Data

May 2, 1991 [DE] Germany .................. 4114285
Jul. 25, 1991 [DE] Germany .................. 4124597

[51] Int. Cl.⁶ .................................. A61C 3/00
[52] U.S. Cl. ........................... 433/19; 433/18
[58] Field of Search ............. 433/7, 18, 19, 21, 22

[56] References Cited

U.S. PATENT DOCUMENTS

| | | | |
|---|---|---|---|
| 3,618,214 | 11/1971 | Armstrong | 433/19 |
| 3,798,773 | 3/1974 | Northcutt | 433/19 |
| 4,382,783 | 5/1983 | Rosenberg | 433/19 |

FOREIGN PATENT DOCUMENTS

| | | |
|---|---|---|
| 0387428 | 9/1990 | European Pat. Off. . |
| 1577599 | 8/1969 | France . |
| 1110363 | 7/1961 | Germany . |
| 380292 | 9/1964 | Switzerland . |

OTHER PUBLICATIONS

Article by Hans Pancherz entitled "Herbst's Hinge" (Das Herbst'sche Scharnier) published by Lunds University, Malmo, Sweden-1983.

*Primary Examiner*—John J. Wilson
*Attorney, Agent, or Firm*—Leydig, Voit & Mayer, Ltd.

[57] ABSTRACT

The invention relates to an apparatus for the forward displacement of the lower jaw, consisting of a telescoping sliding device with a telescope source (1), which is connected via a ball-and-socket joint (5) with a first anchoring band (10) for anchoring on the teeth of a jaw, and with a telescope sleeve (2), which is connected via a second ball-and-socket joint with a second anchoring band for anchoring on the teeth of the counterjaw. So as to embody in such an apparatus the ball-and-socket joints at the ends of the telescoping sliding device with resistance to tension and pressure and nevertheless mountable and removable in a simple way, the invention proposes that the ball insertion openings of the ball sockets (7) of the ball-and-socket joints are aligned substantially perpendicular to the longitudinal extension of the telescope source (1) or telescope sleeve (2), and that the ball head (8) of each ball-and-socket joint (5) is snappable into the associated ball socket (7) under elastic deformation of a safety means (11) with little expenditure of force on part of the user, and, if need be, adapted to be unbuttoned by the user with the help of a detaching instrument.

5 Claims, 3 Drawing Sheets

VENTRAL TELESCOPE

The invention relates to an apparatus for displacing the lower jaw forward, consisting of a telescoping sliding device with a telescope source, which, via a ball-and-socket joint, is connected with a first anchoring band for anchoring on the teeth of a jaw, and with a telescope sleeve, which, via a second ball-and-socket joint, is connected with a second anchoring band for anchoring on the teeth of the counterjaw.

Such ventral telescopes are known, for example from U.S. Pat. No. 3,798,773. For purposes of displacing the lower jaw forward, they are incorporated in the known way in the mouth of the patient orally or vestibularly on the left and right sides. For this purpose, the anchoring bands are fastened on suitable teeth or groups of teeth of the upper and lower jaws. The known ventral telescopes of the above type, because of the ball-and-socket joints used, have the advantage that the lower jaw retains a certain freedom of movement relative to the upper jaw also laterally. However, the known ventral telescopes of the specified type have the drawback that the ball-and-socket joints used therewith can transmit at the end of the telescoping sliding device only pressure forces, but not also tensile forces. So that the balls will not detach themselves from the ball sockets at an inappropriate time, the telescoping sliding device of the known apparatuses is always loaded by a pressure spring disposed interior of the sliding device, which spring always generates a force acting in the extension sense. Said force always presses the balls of the ball-and-socket joints into the associated ball sockets.

However, said continuously acting force, which stresses the jaws of the patient in the opening sense, is often not desired under the medical aspect. It is better from the medical viewpoint if the telescoping sliding device of the ventral telescope only guides the lower jaw relative to the upper jaw along a desired path of movement, but not always exerts a force on the jaws in the opening sense.

With an embodiment of the ball-and-socket joints that is resistant to pressure and tension, mounting and removal of the telescoping sliding device, for example for the purpose of adjustment of the length, or for cleaning and disinfecting by the treating physician is made decisively more difficult. Therefore, due to the difficult mounting and removal, there is the danger of iatrogenic damage in the zone of the corners of the mouth of the patients.

It is, therefore, the problem of the invention to further develop the apparatus of the type specified above in that the ball-and-socket joints at the ends of the telescoping sliding device are embodied with resistance to tension and pressure, but nevertheless mountable and removable by the treating physician in the simplest way.

For resolving said problem, the invention proposes based on the apparatus of the type specified above that the ball insertion openings of the ball sockets of ball-and-socket joints are aligned substantially perpendicular to the longitudinal extension of the telescope source, or telescope sleeve, and that the ball head of each ball-and-socket joint is snappable into the associated ball socket under elastic deformation of a safety means.

The apparatus according to the invention has the advantage that the ball-and-socket joints are both resistant to pressure and sufficiently resistant to tension. Because of the special alignment of the ball insertion openings of the ball sockets of the ball-and-socket joints, tensile forces in the longitudinal direction of the telescoping sliding device practically cannot pull the ball heads from the associated ball sockets. In spite of the largely tension-resistant embodiment in the longitudinal direction of the telescoping sliding device, the ball-and-socket joints can be easily mounted and removed by the treating physician with the help of a suitable instrument, namely without stressing the teeth and the anchoring bands in any excessive way, or without damaging the corners of the mouth of the patients.

According to a first embodiment of the invention, provision is made that the elastic safety means is embodied as a spring ring, which is inserted in a groove in the interior of the ball socket.

According to another advantageous embodiment of the invention, provision is made that the circular edge of the ball insertion opening of the casing of the ball sockets is embodied elastically yielding in the radial direction, and that it has a diameter slightly smaller than the diameter of the ball head. In this way, it is possible to dispense with the spring ring inserted in the groove. The circular edge of the ball insertion opening, on snapping of the ball head into the ball socket, places itself against the surface of the ball head, which makes the ball-and-socket joint run particularly smoothly, and the mounting and the removal of the ball-and-socket joint are simplified.

According to a useful embodiment of the design of the invention discussed last, provision is made that the casing of the ball-and-socket joints consists of an elastic metal alloy, in particular of stainless steel, and that the circular edge of the casing is joined as one piece with the body of the casing, and provided with radial slots distributed across the circumference. The radial slots subdivide the circular edge of the casing in individual elastic segments, which rest against the surface of the ball like elastic tongues. If need be, said tongues can be deformed in a suitably shaped instrument in the sense of a diameter reduction of the circular edge after the ball head has been inserted, which leads to an even safer support of the ball head in the ball socket. According to another embodiment of the invention, provision is made that the edge of the ball insertion opening of the casing is formed by a collar made of an elastic material, which surrounds the casing totally or partly. For producing such an elastic collar, considered are, of course, primarily elastomers that are insensitive to body fluids. With this embodiment of the invention, the ball heads of the ball-and-socket joints are treated with special care. Moreover, it is possible to use for the other components of the casing, and in particular for the ball socket a particularly hard and, if need be, even non-elastic material, which enhances the resistance of the ball-and-socket joint to wear further.

For facilitating the removal of the ball-and-socket joints, provision is made according to another embodiment that the casing is provided within the zone of the bottom of the socket of the ball-and-socket joint with an opening for attaching a detaching instrument. In this insertion duct, a detaching instrument can be inserted, which instrument places itself against the surface of the ball head and forces the latter from the casing, overcoming the resetting forces of the elastic safety means.

The opening may extend, for example crosswise relative to the direction of insertion of the ball head. A wedge-shaped detaching instrument can be inserted in said opening, which forces the ball head from the ball socket.

Finally, so that the telescoping sliding device can be adjusted to the requirements lengthwise, provision is made that the telescope source or the telescope sleeve is provided with a telescope attachment, which is axially adjustable by a screw thread and connected with one of the ball-and-socket joints, whereby the telescope source and the telescope sleeve are guided on one another with torsional resistance. An axial adjustment possibility for finely adjusting the length of the telescoping sliding device is basically known from U.S. Pat. No. 3,798,773, which is part of the state of the art. However, with the latter, there is the risk that the parts of the telescoping sliding device may rotate relative to the telescope attachment around their longitudinal axis at an inappropriate time, so that the length of the telescoping sliding device changes on its own. For said reason, with the apparatus known according to the state of the art, provision must be made for a costly safety device for the thread to avoid rotation. With the embodiment of the invention discussed last, on the other hand, such unintended changes in the length are impossible because any rotation around the longitudinal axis of the telescoping sliding device is impossible due to the special alignment of the ball insertion openings in the zone of the ball-and-socket joints, on the one hand, and because the parts of the telescoping sliding device are nonrotatably guided on each other. Hence any change in length of the telescoping sliding device is possible only in the dismantled condition, and any automatic change in length is excluded.

The invention is explained in greater detail in the following by reference to the drawing, in which.

Figure 1:
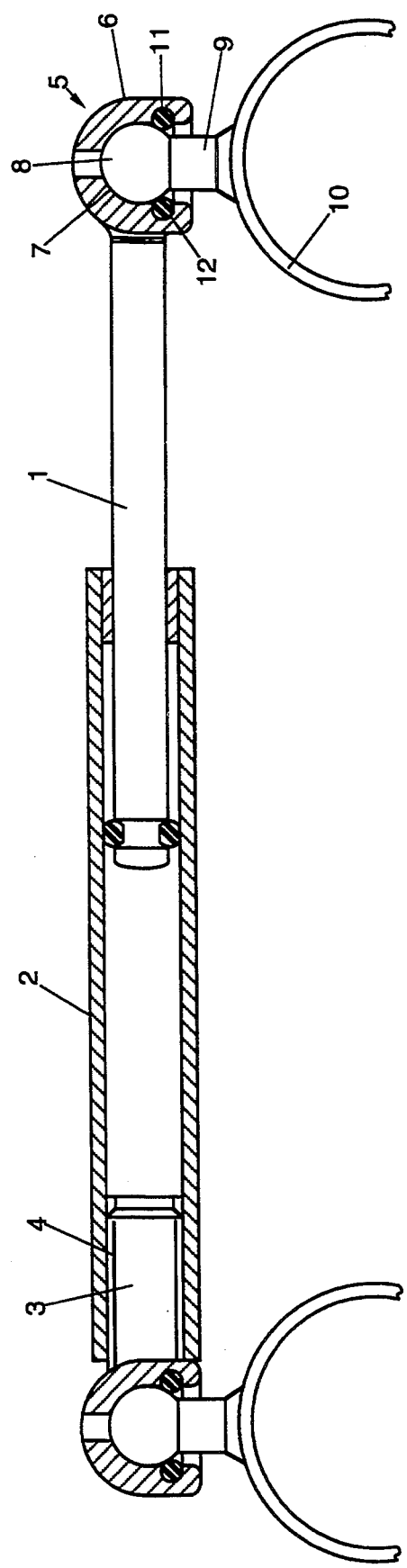
FIG. 1 shows schematically a longitudinal section through the ventral telescope in a first embodiment.

The ventral telescope shown in FIG. 1 has a telescope source 1, a telescope sleeve 2, and a telescope attachment 3. The telescope attachment 3 is axially adjustable vis-a-vis the telescope sleeve 2 by means of a thread 4. Said adjustability serves for the fine adjustment of the length of the telescope in order to be able to adjust the forward displacement of the lower jaw by an exactly defined amount. The telescope source 1 is axially displaceable in the telescope sleeve 2 and supported nonrotatably. At the free end of the telescope source 1, a ball-and-socket joint is present, which in its entirety is denoted by the reference numeral 5. The ball-and-socket joint 5 consists of a casing 6, which in its interior is provided with a ball socket 7. A ball head 8 extends into the casing 5, which ball head is provided with an attachment 9 projecting from the ball insertion opening of the casing 5, said attachment in turn being connected with an anchoring band 10, which serves for anchoring on the teeth of the lower or upper jaw. The ball insertion opening of the ball socket 7 is aligned substantially perpendicular to the longitudinal axis of the telescope source 1, or of the telescope sleeve 2. In this connection, deviations from the exactly perpendicular alignment may only be to a degree that forces acting in the longitudinal direction of the telescope source 1 or telescope sleeve 2 cannot pull the ball head 8 from the joint socket 7. For securing the ball head 8 in the ball socket 7, provision is made on the inside of the casing 6 for an annular groove 11, in which a spring ring (12) is inserted. Said spring ring 12 has an inside diameter smaller than the outside diameter of the ball head 8. For this reason, it widens when the ball head 8 is inserted, so that the latter, on insertion, snaps into the casing 5, and is pressed by the spring ring 12 against the ball socket 7.

The casing 6 of the ball socket 8, on its side opposite the insertion opening, is provided with an opening 6a for inserting a detaching instrument for forcing the ball head 8 from the joint socket 7.

The telescope attachment 3, too, is connected with a ball-and-socket joint which, in its structure, corresponds with the ball-and-socket joint 5 explained above, so that it needs not to be explained again.

Deviating from the exemplified embodiment shown in FIG. 1, the casing 6 and the ball head 8 may be arranged also in the reverse way. In this case, the casing 6 is connected with the anchoring band 10, whereas the ball head 8 is connected with the telescope source 1, or with the telescope attachment 3.

Figure 2:
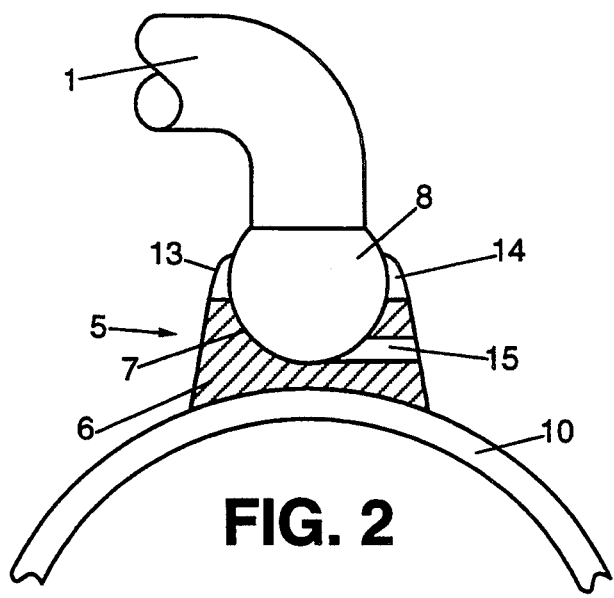
FIG. 2 shows a horizontal section through the ball-and-socket joint in a second embodiment.
Figure 3:
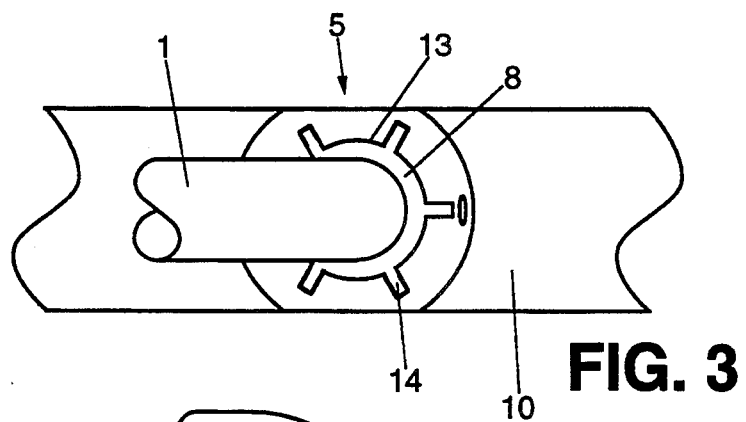
FIG. 3 is a top view of the ball-and-socket joint according to FIG. 2.
Figure 4:
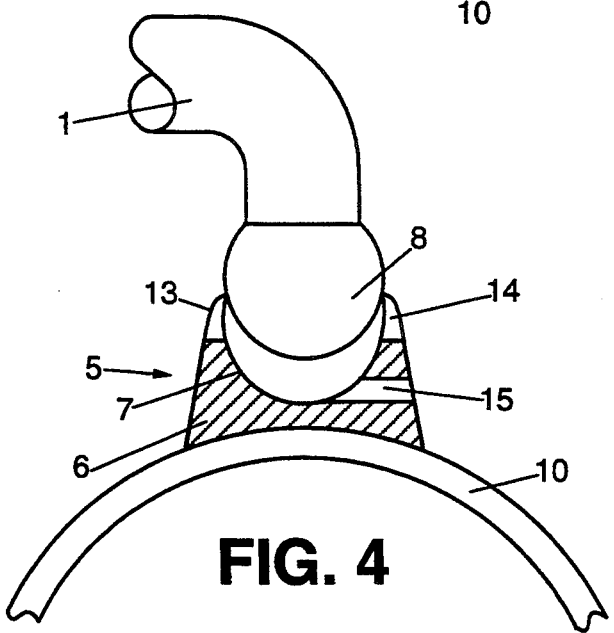
FIG. 4 shows the ball-and-socket joint according to FIG. 2 during mounting/removal.

In the exemplified embodiment shown in FIGS. 2 to 4, the casing 5 connected with the anchoring band 10 has an upper edge 13, of which the inside diameter is slightly smaller than the outside diameter of the ball head 8. The edge 13 is subdivided in individual segments by radially extending slots 14 arranged distributed over the circumference, said segments in a way forming elastically springy tongues which, after the ball head 8 has snapped into the ball socket 7, rest against the ball surface of the ball head. In this connection, said springy tongues of the edge are interiorly shaped in such a way that they support themselves with a large surface on the surface of the ball head 8.

The casing 5 and the elastic edge 13 are preferably manufactured as one piece from stainless steel having the required elastic properties.

As shown in FIG. 2, the casing 5 is provided in the zone of the socket bottom of the ball socket 7 with an opening 15 for a detaching instrument, said opening extending crosswise relative to the direction of insertion of the ball head 8. It is possible to insert in said opening 15, for example a wedge-shaped instrument, which permits forcing the ball head 8 from the casing under elastic deformation of the edge 13 upwardly.

FIG. 4 shows the ball head 8 during the mounting or removal operation, namely in the position in which the elastic edge 13 is elastically widened the most.

Figure 5:
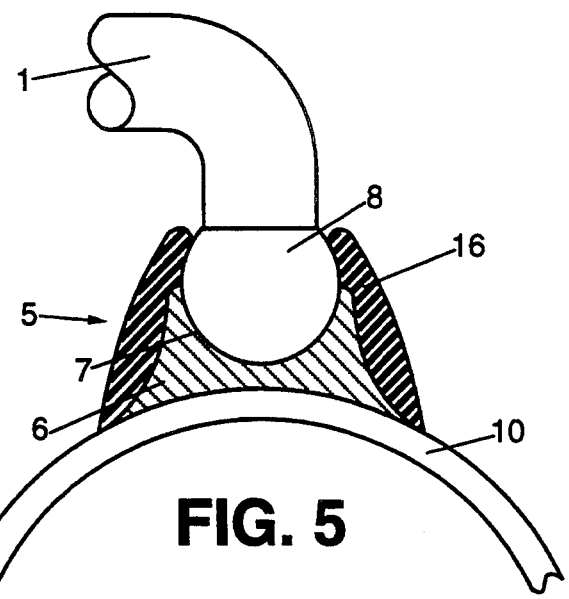
FIG. 5 shows a horizontal section through the ball-and-socket joint in a third embodiment.
Figure 6:
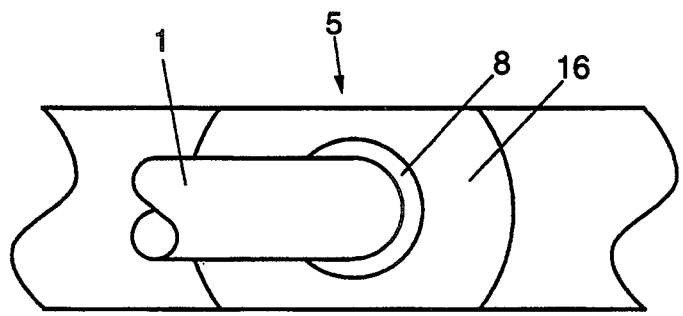
FIG. 6 is a top view of FIG. 5.
Figure 7:
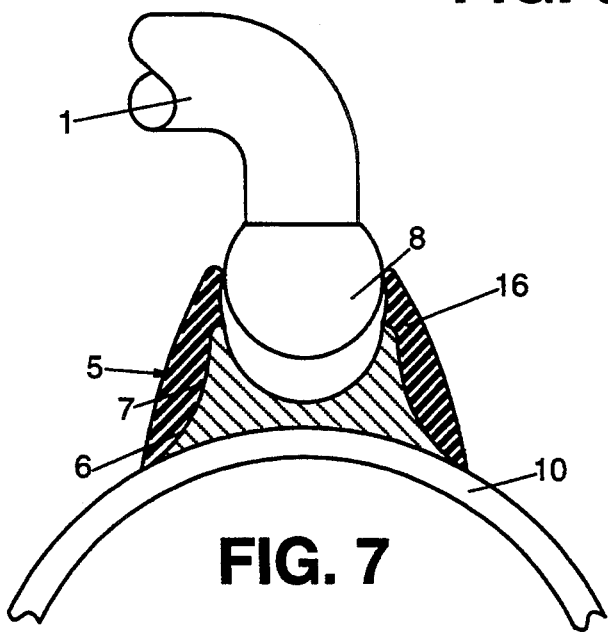
FIG. 7 shows the ball-and-socket joint according to FIG. 5 during mounting/removal.

In the exemplified embodiment according to FIGS. 5 to 7, the elastic edge of the casing is formed by a collar 16 made of an elastically expandable material, said collar surrounding the casing. As elastically expandable material, all elastomers can be considered which possess adequately elastic properties, and which are resistant to body fluids. As an elastic plastic material is substantially more extendible than steel, the slots in the zone of the edge can be dispensed with in the present case. As shown in FIG. 5, in this case too, the elastic collar 16 made of plastic material fits closely with a large surface area to the ball surface of the ball head 8, so that in this exemplified embodiment too, only little wear is caused on the ball head 8.

FIG. 7 shows for this exemplified embodiment too the ball head 8 during the mounting or removal operation, namely in the position in which the collar 16 is elastically widened the most.

I claim:

1. Apparatus for the forward displacement of the lower jaw, said apparatus comprising a telescoping sliding device comprising a first telescoping member having a first ball-and-socket joint means for attaching said first telescoping member to a first anchoring means to be anchored to one or more teeth of a jaw, and a second telescoping sleeve member having a second ball-and-socket joint means for attaching said second member to a second anchoring means to be anchored to one or more teeth of the counterjaw, said socket portion of each of said first and said second ball-and-socket joint means having a ball insertion opening aligned substantially perpendicular to the longitudinal extension of said telescoping members, and said ball portion of each of said first and said second ball-and-socket joint means having a head which is snappable into the respective socket portion of each of said first and said second ball-and-socket joint means under elastic deformation of a safety means, said safety means comprising a spring ring inserted in a groove in the interior of the socket portion of each of said first and said second ball-and-socket joint means.

2. The apparatus according to claim 1, said socket portion of each of said first and said second ball-and-socket joint means having an opening to provide access for a detaching instrument.

3. The apparatus according to claim 2, wherein said opening for said detaching instrument extending crosswise relative to the direction of insertion of said head of said ball portion of each of said first and said second ball-and-socket joint means.

4. Apparatus for the forward displacement of the lower jaw, comprising a telescoping sliding device comprising a first telescoping member having a first ball-and-socket joint means for attaching said first member to a first anchoring means to be anchored to one or more teeth of a jaw, and a second telescoping sleeve member having a second ball-and-socket joint means for attaching said second member to a second anchoring means to be anchored to one or more teeth of the counterjaw, said socket portion of each of said first and said second ball-and-socket joint means having a ball insertion opening aligned substantially perpendicular to the longitudinal extension of said telescoping members, and said ball portion of said ball-and-socket joint means having a head which is snappable into said respective socket portion of said first and said second ball-and-socket joint means under elastic deformation of a safety means, and said ball insertion opening of said socket portion of each of said first and said second ball-and-socket joint means having a circular edge capable of elastically yielding in the radial direction, said circular edge further having a diameter slightly smaller than the diameter of said head of said ball portion of said first and said second ball-and-socket joint means.

5. The apparatus according to claim 4, said circular edge of said ball insertion opening comprising a collar wholly or partly surrounding said socket portion of each of said first and said second ball-and-socket joint means, said collar being constructed of an elastically extendible material.

* * * * *